United States Patent [19]

Lee

[11] Patent Number: 4,523,471
[45] Date of Patent: Jun. 18, 1985

[54] COMPOSITE TRANSDUCER STRUCTURE

[75] Inventor: Paul P. Lee, Littleton, Colo.

[73] Assignee: Biosound, Inc., Indianapolis, Ind.

[21] Appl. No.: 425,216

[22] Filed: Sep. 28, 1982

[51] Int. Cl.³ ............................................. G01N 29/00
[52] U.S. Cl. ...................................... 73/626; 310/334
[58] Field of Search ................. 73/626, 609, 632, 625, 73/628, 641, 618; 367/155, 103; 128/660, 661, 662, 663; 310/334, 366, 357

[56] References Cited

U.S. PATENT DOCUMENTS

| 2,875,355 | 2/1959 | Petermann | 310/366 X |
|---|---|---|---|
| 2,875,607 | 3/1959 | Boxcer et al. | |
| 2,896,098 | 7/1959 | Boxcer et al. | |
| 3,019,636 | 2/1962 | Henry | |
| 3,327,286 | 10/1965 | Dorr et al. | |
| 3,616,682 | 11/1971 | Golis et al. | |
| 3,922,572 | 11/1975 | Cook et al. | |
| 4,096,755 | 6/1978 | Hause et al. | 73/618 X |
| 4,155,259 | 5/1979 | Engeler | 73/626 |
| 4,180,792 | 12/1979 | Lederman et al. | |
| 4,241,611 | 12/1980 | Specht et al. | |
| 4,305,014 | 12/1981 | Borburgh | 310/334 |
| 4,354,132 | 10/1982 | Borburgh | 310/334 |
| 4,398,116 | 8/1983 | Lewis | 310/334 |

Primary Examiner—Stephen A. Kreitman
Assistant Examiner—Vincent P. Kovalick
Attorney, Agent, or Firm—Woodard Weikart, Emhardt & Naughton

[57] ABSTRACT

An ultrasonic transducer in which a plurality of elements are employed alternate ones of which are utilized as transmitters and receivers and having the same area but in which the transmitter elements are composed of material having a high transmit sensitivity while the receiver elements are composed of a material having a high receive sensitivity.

5 Claims, 2 Drawing Figures

COMPOSITE TRANSDUCER STRUCTURE

BACKGROUND OF THE INVENTION

This invention relates to ultrasonic imaging, or doppler and more particularly to an improved transducer structure useful in ultrasonic imaging or doppler, especially in the area of medical diagnosis.

Ultrasonic transducers are well known in the art and a large variety of shapes and sizes have been proposed. One particularly useful configuration for medical diagnosis is an annular array wherein one or more ring shaped transducing elements are arranged in concentric fashion about an axis in order to pulse energy into a body and to receive the reflected energy from internal organs. An example of such a transducer may be found in the Specht et al. U.S. Pat. No. 4,241,611, issued Dec. 30, 1980. This patent also notes that one of the rings may be dedicated to transmit energy while the remainder of the rings may be used to receive energy. Also, if the transmit ring is a separate ring, it can then be made of a different material which is more efficient as a transmitter than as a receiver. The Dorr et al. U.S. Pat. No. 3,327,286 issued June 30, 1967 also shows a sonic transducer having two annular elements one of which is a transmitter and the other of which is a receiver.

The difficulty with the prior art has been the problem of obtaining increased sensitivity without having beam pattern degradation. More specifically, it is desirable to have a beam pattern which is substantially symmetrical at all depths at which the transducer is to be used. I have determined that one way of obtaining this desired beam pattern is to construct a transducer array in which alternate ones of the transducer elements transmit radiation while the opposite alternate ones receive the reflected radiation and the area of all of the elements is substantially the same. Furthermore, by constructing a tranducer in this manner and utilizing a material for the transmitting elements which is chosen for high transmit sensitivity and utilizing a different material chosen for high receive sensitivity for the receiving elements an increase of sensitivity results.

SUMMARY OF THE INVENTION

The present invention increases the sensitivity of an ultrasonic transducer without losing beam pattern symmetry by utilizing elements which are alternately arranged as transmitters and receivers, all of which are of substantially the same area in order to obtain a good beam pattern and in which the transmitters are composed of material which has a high transmit sensitivity while the receivers are composed of a slightly different material which has a high receive sensitivity.

DETAILED DESCRIPTION OF THE PREFERRED EMBODIMENT

Figure 1:
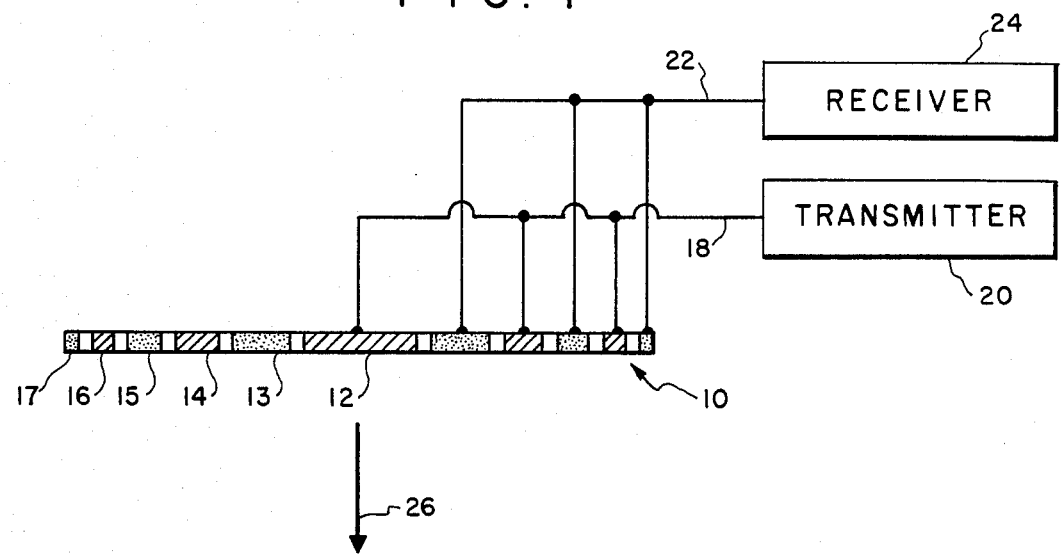
FIG. 1 is a cross-sectional view of an ultrasonic transducer constructed in an annular arrangement.
Figure 2:
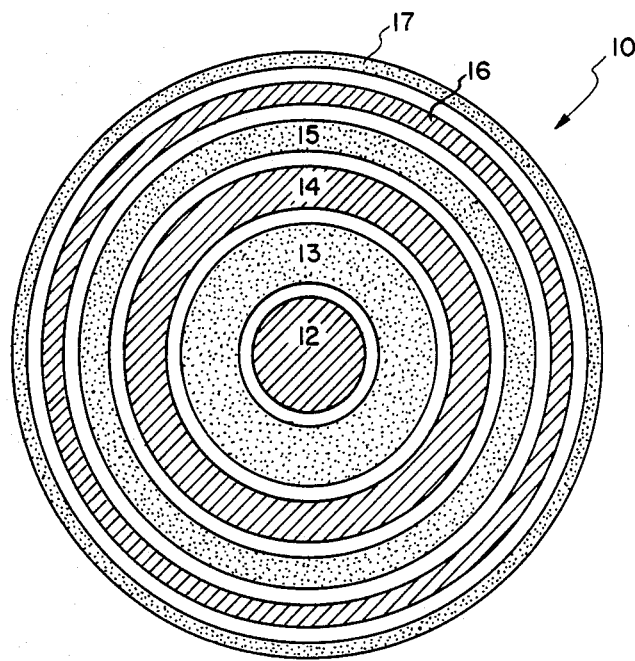
FIG. 2 is a top view of the transducer of FIG. 1.

FIGS. 1 and 2 show an ultrasonic transducer 10 consisting of a plurality of transducing elements 12, 13, 14, 15, 16, and 17, arranged as concentric rings in an annular array. The area of each of the elements is substantially the same as can be seen in FIGS. 1 and 2 by the fact that the width of the elements decreases as the distance from the center increases.

Alternate ones of the elements, e.g., 12, 14, and 16 are connected together by conductor 18 to a transmitter 20. The other alternate ones of the elements, e.g., 13, 15, and 17 are connected together by a conductor 22 to a receiver 24. Upon a signal from transmitter 20 elements 12, 14, and 16 transmit a pulse of ultrasonic energy in a general direction shown by arrow 26 to a remotely located object such as the internal parts of a body. Reflections from the internal parts are received by elements 13, 15, and 17 and are presented to receiver 24 for use thereby in an imaging system (not shown) which may be like that described in the James M. Gessert co-pending application, Ser. No. 173,874, filed July 30, 1980. Since the area of elements 12, 13, 14, 15, 16, and 17 are substantially the same, the beam pattern of the energy transmitted and received by the transducer 10 remains symmetric throughout the range of depth for which the transducer is to be used. In order to increase sensitivity, however, elements 12, 14, and 16 are made from a material which has high transmit sensitivity even though such material may have a low receive sensitivity while elements 13, 15, and 17 are made from a material which has high receive sensitivity even though such material may have a rather low transmit sensitivity. By this means the transmitter sensitivity is increased and the receiver sensitivity is increased without a loss of beam pattern symmetry. An example of a material having high transmit sensitivity is lead zirconate lead titinate (PZPT) comprising approximately fifty-three percent lead zirconate and approximately forty-seven percent lead titinate and which utilizes a lanthanum oxide dopant. An example of a material having high receive sensitivity is PZPT consisting of about sixty-five percent lead zirconate and about thirty-five percent lead titinate with a niobium oxide dopant. Other materials will occur to those skilled in the art.

While the present invention has been shown in connection with an annular array of transducing elements, it should be understood that a linear array in which alternate elements are transmitters and receivers but in which all of the elements have the same area and in which the receivers and transmitters utilize high receive sensitivity and high transmit sensitivity materials respectively could be employed. I therefore do not wish to be limited by the disclosures used in connection with the preferred embodiment, but wish to be limited only by the following claims.

I claim:

1. An ultrasonic transducer comprising:
    means for transmitting an ultrasonic energy pulse beam into an object region, said transmitting means including a first plurality of transducer elements, each of which is constructed of a material which is sensitive to ultrasonic energy and is higher in transmit sensitivity than receive sensitivity;
    means for receiving an echo pulse beam produced by said transmitting means and reflected from said object region, said receiving means including a second plurality of transducer elements, each of which is constructed of a material which is sensitive to ultrasonic energy and is higher in receive sensitivity than transmit sensitivity;
    means mounting transducer elements for the first plurality alternately with and laterally arranged relative to the transducer elements of the second plurality; and said transducer elements of said first plurality of transducer elements being fabricated of a material which is about fifty-three percent lead zirconate and about forty-seven percent lead titinate doped with lanthanum oxide and said transducer elements of said second plurality of transducer elements is fabricated of a material which is about sixty-five percent lead zirconate and about thirty-five percent lead titinate doped with niobium oxide.

2. The ultrasonic transducer of claim 1 wherein the transducer elements of both the first and second plurality of transducer elements are ring-shaped and said mounting means mounts the transducer elements annularly.

3. The ultrasonic transducer of claim 2 wherein all of the transducer elements of said first and second plurality of transducer elements all have substantially the same area.

4. The ultrasonic transducer of claim 2 which further includes connection means for connecting the transducer elements of the first plurality of trnsducer elements to an ultrasonic transmitter and for connecting the transducer elements of said second plurality of transducer elements to an ultrasonic receiver.

5. An ultrasonic transducer comprising:

means for transmitting an ultrasonic energy pulse beam into an object region, said transmitting means including a first plurality of transducer elements, each of which is constructed of a material which is sensitive to ultrasonic energy and is higher in transmit sensitivity than receive sensitivity;

means for receiving an echo pulse beam produced by said transmitting means and reflected from said object region, said receiving means including a second plurality of transducer elements, each of which is constructed of a material which is sensitive to ultrasonic energy and is higher in receive sensitivity than transmit sensitivity;

means mounting transducer elements for the first plurality alternately with and laterally arranged relative to the transducer elements of the second plurality;

said transducer elements of both the first and second plurality of transducer elements are ring-shaped and said mounting means mounts the transducer elements annularly and wherein all of the transducer elements of the first and second plurality of transducer elements have substantially the same area;

connection means for connecting the transducer elements of the first plurality to an ultrasonic transmitter and for connecting the transducer elements of the second plurality to an ultrasonic receiver; and said transducer elements of the first plurality of transducer elements is fabricated from a material which is about fifty-three percent lead zirconate and about forty-seven percent lead titinate doped with lanthanum oxide and said transducer elements of the second plurality of transducer elements is fabricated of a material which is about sixty-five percent lead zirconate and about thirty-five percent titinate doped with niobium oxide.

* * * * *